(12) United States Patent
Penth et al.

(10) Patent No.: US 8,584,505 B2
(45) Date of Patent: Nov. 19, 2013

(54) MEASURING INSTRUMENT AND METHOD FOR DETECTING THE CONTENT OF OIL, HYDROCARBONS AND OXIDIZABLE GASES IN AIR OR COMPRESSED AIR

(75) Inventors: Bernd Penth, Lebach (DE); Max Penth, Lebach (DE); Felix Penth, Lebach (DE)

(73) Assignee: Synthesechemie Dr. Penth GmbH, Lebach (DE)

( * ) Notice: Subject to any disclaimer, the term of this patent is extended or adjusted under 35 U.S.C. 154(b) by 227 days.

(21) Appl. No.: 13/138,079

(22) PCT Filed: Jan. 5, 2010

(86) PCT No.: PCT/DE2010/075000
§ 371 (c)(1),
(2), (4) Date: Jul. 1, 2011

(87) PCT Pub. No.: WO2010/075858
PCT Pub. Date: Jul. 8, 2010

(65) Prior Publication Data
US 2011/0265550 A1 Nov. 3, 2011

(30) Foreign Application Priority Data
Jan. 5, 2009 (DE) .................. 10 2009 004 278

(51) Int. Cl.
*G01N 7/00* (2006.01)
(52) U.S. Cl.
USPC .......................................... 73/23.2; 436/143
(58) Field of Classification Search
USPC ........ 73/23.2, 23.32, 23.33, 28, 28.01, 29.01, 73/31.01–31.03; 422/83, 93; 436/139–143
See application file for complete search history.

(56) References Cited

U.S. PATENT DOCUMENTS

| 3,652,227 A | * | 3/1972 | Harman et al. | ............... 436/118 |
| 3,692,492 A | * | 9/1972 | Poli, Jr. et al. | .................. 422/54 |

(Continued)

FOREIGN PATENT DOCUMENTS

| DE | 24 07 940 | 9/1974 |
| DE | 33 12 525 | 11/1983 |

(Continued)

OTHER PUBLICATIONS

DIN ISO 8573-2, Compressed Air and Gas Institute, Aug. 19, 2005, total of 27 pages. (Spec, p. 2).

(Continued)

*Primary Examiner* — Leonard Chang
*Assistant Examiner* — Natalie Huls
(74) *Attorney, Agent, or Firm* — Collard & Roe, P.C.

(57) ABSTRACT

The invention relates to a measuring instrument and method for detecting the content of oil, hydrocarbons and oxidizable gases in air or compressed air.
In order to develop a measuring instrument for detecting the content of oil, hydrocarbons and oxidizable gases in air or compressed air, said instrument being suitable for detecting concentrations in the lower $\mu g/m^3$ range or in the ppb range and allowing measuring accuracy of 10 micrograms oil/$m^3$ air at a measurement error in the single-digit percentage range, it is proposed according to the invention that the measuring instrument comprises an air or compressed-air connection and, connected thereto, a flow limiter to which a catalyst is connected that is connected in turn with a photoionization detector, switchable means being provided for routing the air or compressed air over the oxidation catalyst or past it directly to the photoionization detector.

9 Claims, 11 Drawing Sheets

(56) References Cited

U.S. PATENT DOCUMENTS

Figure 1:
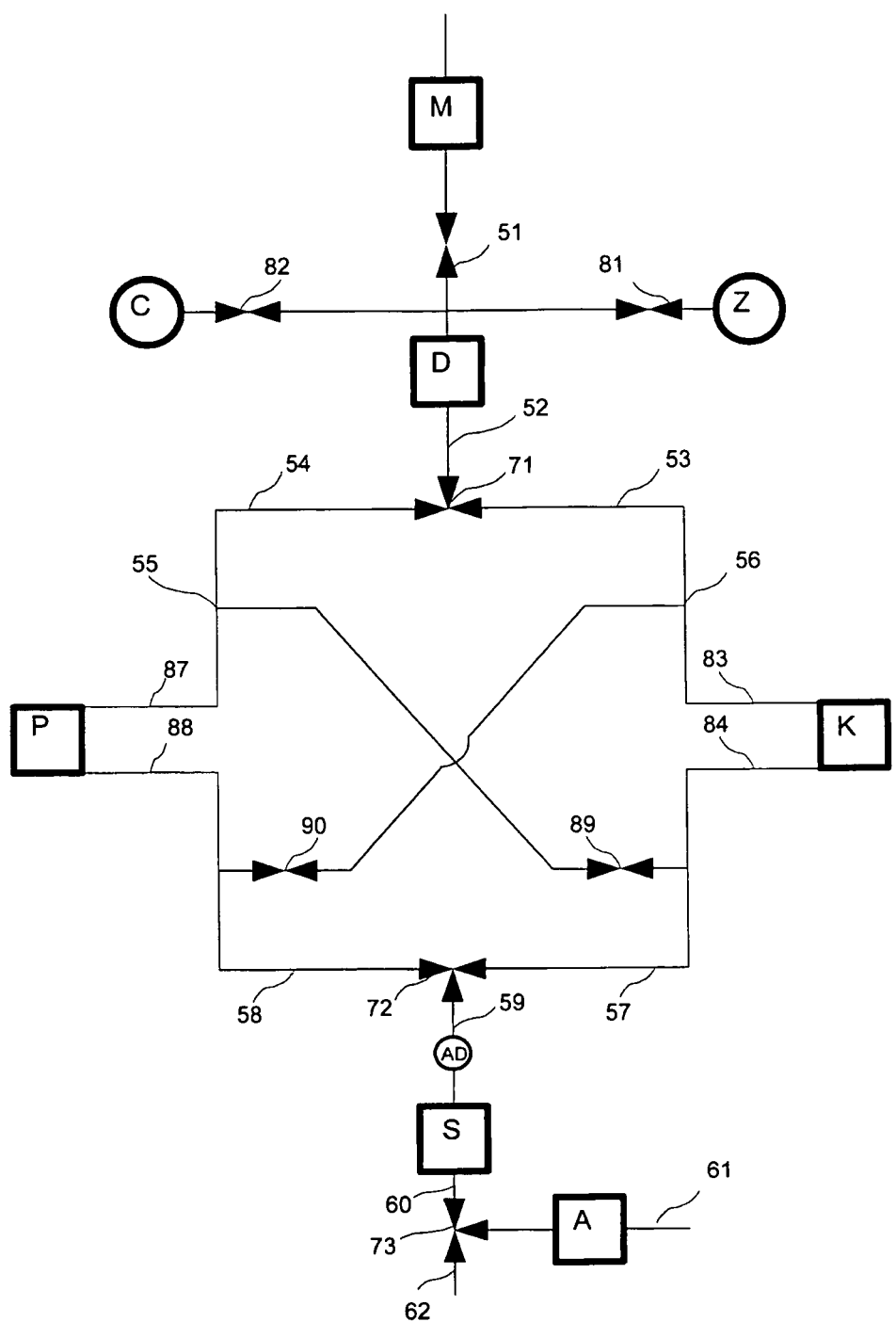

| | | | | |
|---|---|---|---|---|
| 3,762,878 | A | * | 10/1973 | Villalobos ................ 436/143 |
| 3,933,432 | A | | 1/1976 | Driscoll |
| 3,943,751 | A | * | 3/1976 | Akiyama et al. ........... 73/25.03 |
| 4,004,882 | A | * | 1/1977 | Byrne et al. .................. 422/83 |
| 4,063,446 | A | * | 12/1977 | Fuhrmann ................. 73/31.02 |
| 4,102,648 | A | * | 7/1978 | Hartmann et al. ............. 422/54 |
| 4,384,471 | A | * | 5/1983 | Wentzel ..................... 73/23.38 |
| 4,555,931 | A | * | 12/1985 | Amimoto et al. ............. 73/23.2 |
| 4,891,186 | A | | 1/1990 | Roberge et al. |
| 5,265,031 | A | | 11/1993 | Malczewski |
| 5,654,498 | A | * | 8/1997 | Kessel ....................... 73/31.07 |
| 5,665,902 | A | * | 9/1997 | Wang et al. ............... 73/28.01 |
| 5,894,083 | A | * | 4/1999 | Hiraoka et al. ............... 73/23.2 |
| 5,968,837 | A | * | 10/1999 | Doring et al. ............... 436/173 |
| 6,000,275 | A | * | 12/1999 | Nishina et al. ............. 73/31.03 |
| 7,223,607 | B2 | * | 5/2007 | Bryselbout ................. 436/139 |
| 7,255,836 | B2 | * | 8/2007 | Lehmann et al. ............. 422/83 |
| 7,931,467 | B2 | * | 4/2011 | Schilling et al. .............. 431/89 |
| 2002/0021984 | A1 | * | 2/2002 | Kroneisen ..................... 422/83 |
| 2003/0200796 | A1 | * | 10/2003 | Pawliszyn ................. 73/64.47 |
| 2007/0051163 | A1 | * | 3/2007 | Wohltjen ................... 73/31.07 |
| 2012/0279277 | A1 | * | 11/2012 | Parusel et al. ................ 73/1.06 |

FOREIGN PATENT DOCUMENTS

| | | | |
|---|---|---|---|
| DE | 41 20 246 | 3/1993 | |
| DE | 691 22 357 | 3/1997 | |
| DE | 196 09 582 | 5/1997 | |
| DE | 197 12 823 | 10/1997 | |
| DE | 198 11 708 | 9/1999 | |
| EP | 467307 A2 | * 1/1992 | ............ G01N 33/00 |
| RU | 2 340 889 | 12/2008 | |

OTHER PUBLICATIONS

DIN ISO 8573-5, Compressed Air—Part 5: Determination of oil vapour and organic solvent content, 2000, total of 15 pages. (Spec, pp. 2, 4, 11 and 17-18).

DIN ISO 8573-1, Compressed Air—Part 1: Contaminants and purity classes, Second Edition, Feb. 1, 2001, total of 16 pages. (Spec, pp. 3-4 and 11).

Dissertation by Nikos Papamichail, "*Residual Oil Monitoring in Pressurised Air with $SnO_2$-based Gas Sensors*," 2004, total of 116 pages. (Spec, p. 4).

International Search Report of PCT/DE2010/075000, Jun. 23, 2010.

* cited by examiner

— Reference   — Air to be analyzed

— Reference   — Air to be analyzed

MEASURING INSTRUMENT AND METHOD FOR DETECTING THE CONTENT OF OIL, HYDROCARBONS AND OXIDIZABLE GASES IN AIR OR COMPRESSED AIR

CROSS REFERENCE TO RELATED APPLICATIONS

This application is the National Stage of PCT/DE2010/075000 filed on Jan. 5, 2010, which claims priority under 35 U.S.C. §119 of German Application No. 10 2009 004 278.4 filed on Jan. 5, 2009, the disclosure of which is incorporated by reference. The international application under PCT article 21(2) was not published in English.

The invention relates to a measuring instrument and method for detecting the content of oil, hydrocarbons and oxidizable gases in air or compressed air.

Various sensor techniques exist for detecting hydrocarbons in air or compressed air. Frequent use is made of electrically heated semiconducting oxides. When these semiconducting oxides are in the heated state, their electrical resistance changes as a function of the hydrocarbon content in the air.

Another method of detecting hydrocarbons is by means of pellistors. To this end, the stream of gas to be analysed is passed over a small bead of heated catalyst material, inside of which a heated platinum coil is located. The hydrocarbon content is measured via the change in electrical resistance of the heated platinum coil or of a second platinum coil, said change being induced by the heat of combustion of the hydrocarbon on the catalyst.

Flame ionisation detectors are also used. Here, hydrocarbons are burned in a stream of gas and the voltage change between two electrodes in the flame measured.

A further method of detecting hydrocarbons is by means of photoionization, which involves irradiating the hydrocarbons with intense ultraviolet light. The light must have enough energy to knock electrons out of the hydrocarbon. The quantity of these electrons can then be measured via two electrodes. For aromatic hydrocarbons, the minimum photon energy required is 8.5 to 9.2 eV, for combustible hydrocarbons at least 9.0 to 12.6 eV.

The measured values generated by photoionization detectors (PIDs) are usually only an indirect indication of the amount of substance measured, as these values are also a function of the compound's formula and can vary substantially even for identical empirical formulae. If the compound being measured is consistent, its identity is known and, if possible, uniform, the hydrocarbon concentration can be measured fairly well.

However, the measuring accuracy decreases as the concentration of hydrocarbons sinks. At the same time, the influence of the air's moisture content, in particular, increases. The influence of moisture in the air thus becomes increasingly higher with decreasing hydrocarbon concentration. It is accordingly impossible to perform sufficiently accurate measurements of hydrocarbon quantities in the lower $mg/m^3$ range and, particularly, in the $\mu g/m^3$ range.

Another problem that makes accurate measurements difficult is the sensor's zero-line drift and the sensitivity drift as a function of time and sometimes also temperature.

Different limiting values for oil content are specified for the various applications of compressed air. Oil fractions are made up of drop-like oil aerosols and of oil vapours. Oil aerosols and oil vapours can be eliminated from a stream of compressed air by various methods.

However, the measurement of oil in compressed air remains a problem that has not yet been solved satisfactorily.

Compressed air streams exist that have high oil contents ranging from well above 10 $mg/m^3$ up to several $g/m^3$ air and consisting primarily of oil aerosols. Due to the droplet character of aerosols, these oil contents can only be measured very unreliably, or not at all, with measuring techniques—for example semiconductor sensors—that are used for hydrocarbon vapours in this concentration range. This is because oil aerosols deposit, in partially or unoxidized form, as tar-like catalyst poison on the sensor.

Other compressed air streams are processed with filters or catalysts to the extent that they are largely free of aerosols, leaving only a gaseous oil fraction in the air stream.

Oils have a low vapour pressure, meaning that concentrations of pure oil vapours are typically below 10 $mg/m^3$ air. However, measuring instruments used to detect hydrocarbon contents, which are usually based on semiconductor sensors or infrared sensors, only measure with acceptable accuracy and reproducibility at concentrations above 10 $mg/m^3$ air.

DIN/ISO 8573-2 and DIN/ISO 8573-5 constitute the state of the art for the discontinuous measurement of oil-containing air. As specified in these standards, aerosols and vapours are deposited in sampling systems on glass fibres and activated charcoal, and the samples sent to a certified laboratory for determination of the oil content.

DE 691 22 357 T2 and U.S. Pat. No. 4,891,186 A cited therein describe the flame-ionization-detector analysis of analyte gases and reference gases, including hydrocarbons, and the evaluation thereof.

DE 33 12 525 A1 describes a device for measuring the separation ratio of branched gas streams.

In DE 41 20 246 A1, the gas to be analysed by a flame ionisation detector is rarefied by means of a mixing apparatus in order to reduce the explosion danger.

DE 24 07 940 A describes a device for simultaneously measuring the proportion of the hydrocarbon fraction with a low boiling point and the total hydrocarbons without this fraction in a gas sample.

The US 2007/0051163 A1 relates to a device for transferring various gas samples to a gas sensor in a detection zone without the sample undergoing any substantial change in pressure.

The admixing of certain reagent gases in a combined photoionization/ion mobility spectrometry system for the detection of substances with a weak proton affinity is known from DE 196 09 582 C2.

DE 197 12 823 A1 describes an infrared gas analyser with an integrated oxidation catalyst that is not described in more detail. To counter major interference by water, a moisture trap is also employed, which can dry the air to be analysed for the purpose of referencing measurements.

In DE 197 12 823 A1 and the previous prior art cited therein, a catalyst and a set of magnetic valves are used as in the invention according to this application. However, the objective, measuring method, procedure, logic circuits and results are completely different.

In order to obtain reliable and acceptable measurements, it is prior art to perform comparative measurements using test gases from gas cylinders. However, test gases are of limited suitability, especially if the hydrocarbon contents to be measured are very low. The reason for this is the increasing influence of air moisture, which often even fluctuates, on the signals obtained for the very low hydrocarbon contents to be measured in the compressed air under analysis. Test gases, by contrast, are always dry or have a constant moisture content.

The influence of moisture can displace the sensor's zero line and also cause a change in measuring sensitivity.

In some industrial sectors, however, DIN ISO 8573-1, by way of example, specifies proof of adherence to a limiting value of 0.01 mg/m$^3$ air for Class 1 compressed air. For Class 0 compressed air, DIN ISO 8573-1 specifies a residual oil content of even less than 0.01 mg/m$^3$ air.

So far, it has not been possible to use known measuring principles and the sensors they involve for this application.

True, attempts have been made to measure the moisture content of the air stream under analysis with a moisture sensor and to process this value in such a way with the value obtained for the hydrocarbon content as to obtain a value which is not influenced by moisture content. In practice, however, this is difficult, because the moisture measurements do not meet the strict accuracy requirements. An additional problem is the influence of temperature change.

The fact that DIN ISO 8573-1 classifies hydrocarbon content in mg/m$^3$ causes difficulty. This is because PID measurements, by contrast, are expressed in ppm, since according to the principle on which a PID sensor works, signal strength is a function of the ratio of the number of parts hydrocarbon to the number of parts air. It is therefore necessary to know which hydrocarbon is to be measured. Furthermore, different hydrocarbons have different response factors. If, for example, a sensor is calibrated with isobutylene and then used, calibrated in this way, to measure a different hydrocarbon, the value obtained must be corrected to take the different response factor and the different molecular weight of the other hydrocarbon into account. However, oils consist of different proportions of a whole series of different hydrocarbons.

A common procedure used currently is to measure hydrocarbons according to DIN ISO 8573-5 using adsorbent collecting tubes. After the adsorption time has elapsed, the content of these tubes is extracted and measured in a certified laboratory. There is thus a long delay before the results of measurements made using these collection tubes are known, with the consequence that oil leaks are often not recognized until long after damage had been done by contaminated lines and products.

Despite many years of manifold endeavours by industry to develop a suitable measuring instrument for measuring oil vapour concentrations of below 1 ppb in compressed air, such an instrument is as yet not commercially available. These unsuccessful endeavours are summarized by way of example in the dissertation "Residual Oil Monitoring in Pressurised Air with SnO$_2$-based Gas Sensors" by N. Papamichail.

One reason why these efforts have failed is that the measuring instrument must, on the one hand, withstand the harsh operating conditions prevailing in an environment generating compressed air and also be intuitively and easily operable, even by untrained personnel, while, on the other hand, it must also provide all the operating functions needed to achieve the required measuring accuracy.

A wide range of portable PID-based measuring instruments is also commercially available, intended, for example, for monitoring tasks in the chemical industry or for use by the fire brigade. The accuracy of these instruments is in the ppm range.

The object of this invention is thus to develop a measuring instrument for detecting the content of oil, hydrocarbons and oxidizable gases in air or compressed air, said instrument being suitable for detecting concentrations in the lower μg/m$^3$ range or in the ppb range and allowing measuring accuracy of 10 micrograms oil/m$^3$ air at a measurement error in the single-digit percentage range.

This object is established according to the invention in that the measuring instrument has an air or compressed-air connection and, connected thereto, a flow limiter to which a thermal oxidation catalyst is connected that is connected in turn with a photoionization detector, switchable means being provided for routing the air or compressed air over the oxidation catalyst or past it directly to the photoionization detector, and that a switchable test-gas inlet (C) is fitted between the air or compressed-air connection (M) and the flow limiter (D).

Alternatively, the object is established in that the measuring instrument has an air or compressed-air connection and, connected thereto, a flow limiter to which a photocatalyst is connected that is connected in turn with a photoionization detector, switchable means being provided for routing the air or compressed air over the photocatalyst or past it directly to the photoionization detector, and that a switchable test-gas intake (C) is fitted between the air or compressed-air connection (M) and the flow limiter (D). Ultraviolet light with a preferable wavelength of 370-385 nm is beamed onto the photocatalyst.

Alternatively, the object may also be established in that the measuring instrument has an air or compressed-air connection and, connected thereto, a flow limiter to which an activated charcoal adsorber is connected that is connected in turn with a photoionization detector, switchable means being provided for routing the air or compressed air over the activated charcoal adsorber or past it directly to the photoionization detector, and that a switchable test-gas intake (C) is fitted between the air or compressed-air connection (M) and the flow limiter (D).

The alternative with the thermal oxidation catalyst was found to be the variant that produces the most accurate results. Energy consumption, however, is comparatively high, making this alternative less suitable for a portable instrument. The alternative with the activated charcoal adsorber is of simple design but comparatively inaccurate and rather maintenance-intensive. The alternative with a photocatalyst requires little maintenance and, thanks to the use of UV LEDs, uses less energy than the thermal oxidation catalyst. It is therefore well suited for portable instruments.

It is within the scope of the invention that a measuring chamber is provided which has, projecting into the centre thereof, a detector input for a photoionization detector, and whose one chamber wall consists of transparent plastic fitted with UV LEDs, that the hollow space formed by the chamber, detector and the transparent plastic wall is smaller than 1 ml and that an opening with a flow resistor is provided for periodically exchanging the gas in the hollow space.

A refinement of the invention consists in that, in addition to the oxidation catalyst, photocatalyst or activated charcoal adsorber, at least one permeator for releasing a temporally constant, defined amount of hydrocarbon is installed, with switchable means being provided for routing the air or compressed air via the permeator or past it directly to the photoionization detector.

It is expedient to fit a switchable test-air inlet between the air or compressed-air connection and the flow limiter.

It is likewise expedient to fit a switchable zero-air inlet between the air or compressed-air connection and the flow limiter.

One embodiment of the invention consists in that a switchable connection to an activated-charcoal tube is provided directly downstream of the photoionization detector.

A preferred embodiment of the invention consists in that an air-moisture compensator is fitted upstream of the photoionization detector.

The scope of the invention also includes a method for detecting the content of oil, hydrocarbons and oxidizable gases in air or compressed air using a measuring instrument according to the invention, a variable proportion of the hydrocarbons being catalytically oxidized and, in this way, dilution series being generated for the purpose of carrying out a referencing measurement while hydrocarbon-containing air or compressed air is being analysed.

The scope of the invention also includes a method for detecting the content of oil, hydrocarbons and oxidizable gases in air or compressed air using a measuring instrument according to the invention, a variable proportion of zero air being mixed with the hydrocarbon-containing air and, in this way, dilution series being generated for the purpose of carrying out a referencing measurement while hydrocarbon-containing air or compressed air is being analysed.

These methods have the advantage that the sensor's response pattern, which may be slightly sinusoidal, is smoothed during the dilution phase by averaging.

Finally, it is also within the scope of the invention that, in order to increase the measuring accuracy, both the hydrocarbon-containing air to be analysed and the catalytically treated air or zero air are enriched by way of the permeator with equal amounts of hydrocarbon so as to shift the measuring range into the linear measuring range.

The solutions found in this invention are not realised in known descriptions and instruments. In particular, for example, these contain no mention of the possibility of using a photocatalyst, generating arbitrary dilution series, using permeation tubes as reference and to increase measuring sensitivity, using a moisture buffer (compensator) and means to identify the optimum valve switch-over time, or the combination of these new possibilities.

PID sensors are generally considered to respond linearly to fluctuating hydrocarbon concentrations. However, measurements performed within the scope of the invention showed that with more accurate measurements in the 10 μg oil/m$^3$ air range, the measurement signal is already substantially weaker. As the concentration continues to decrease, the signal weakens further at a highly disproportional rate.

One requirement was thus to develop and implement a corrective linearity function for the instrument.

However, the corrective linearity function is found to only partially solve the accuracy problem that arises at very low concentrations. As the deviation from linearity is caused by weakening of the signal, amplifying the signal improves the result although noise-related errors must be anticipated.

The invention thus provides a way of eliminating this inaccuracy too, which is caused by a disproportionately weak signal in the 1-10 μg oil/m$^3$ air range.

The invention furthermore provides a portable variant of the measuring instrument, permitting more accurate hydrocarbon measurements in mobile applications.

The invention is explained in detail below by reference to drawings.

Figure 2:
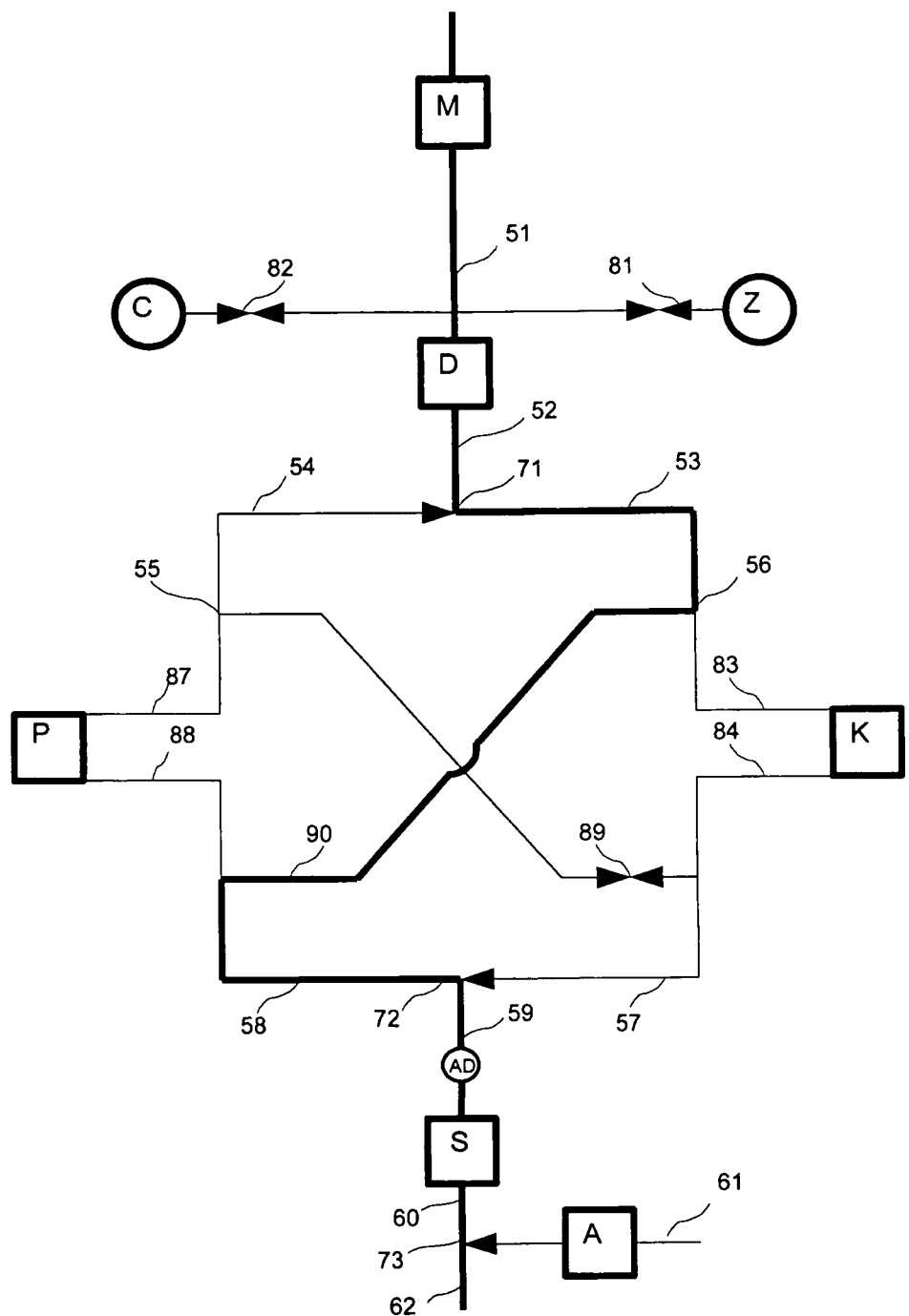
Figure 3:
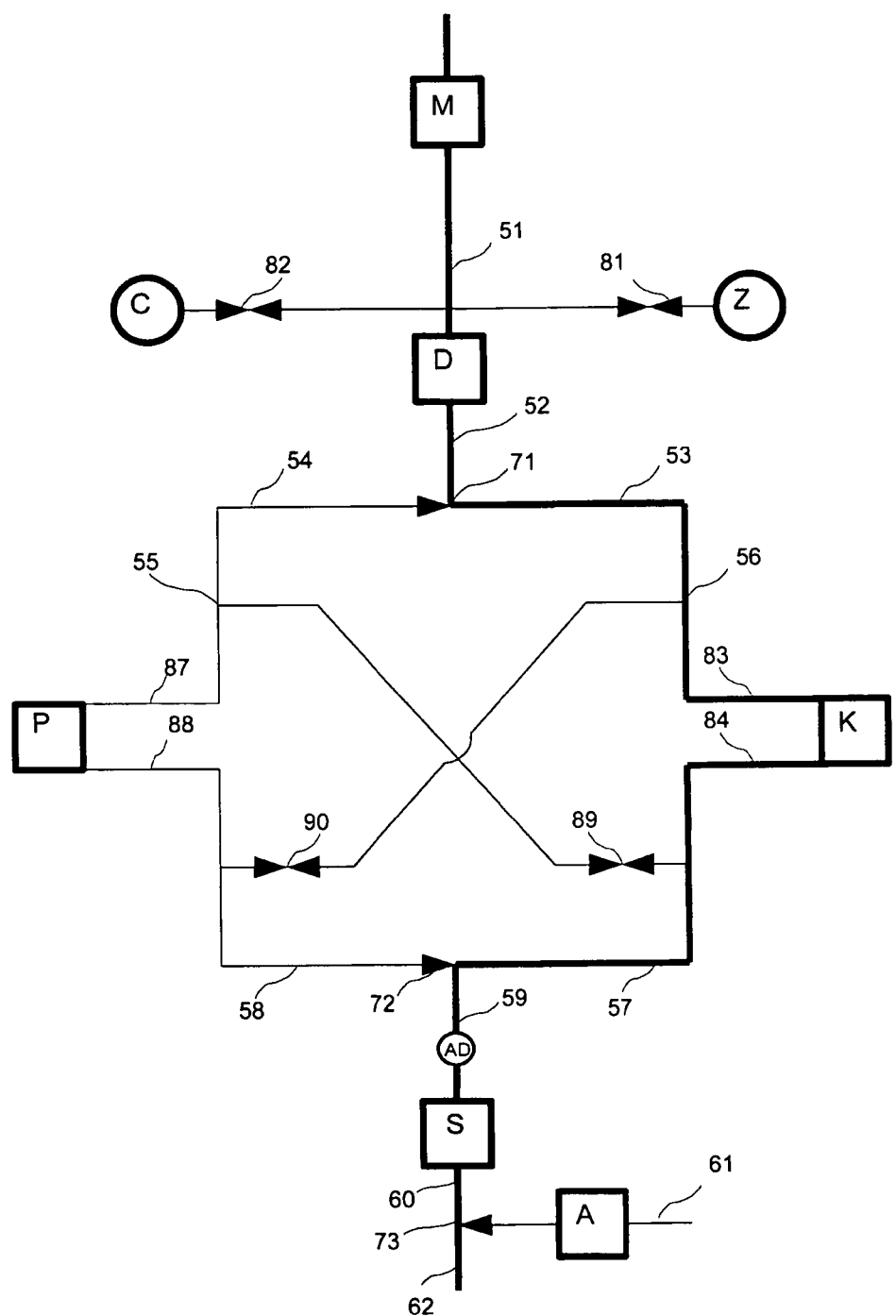
Figure 4:
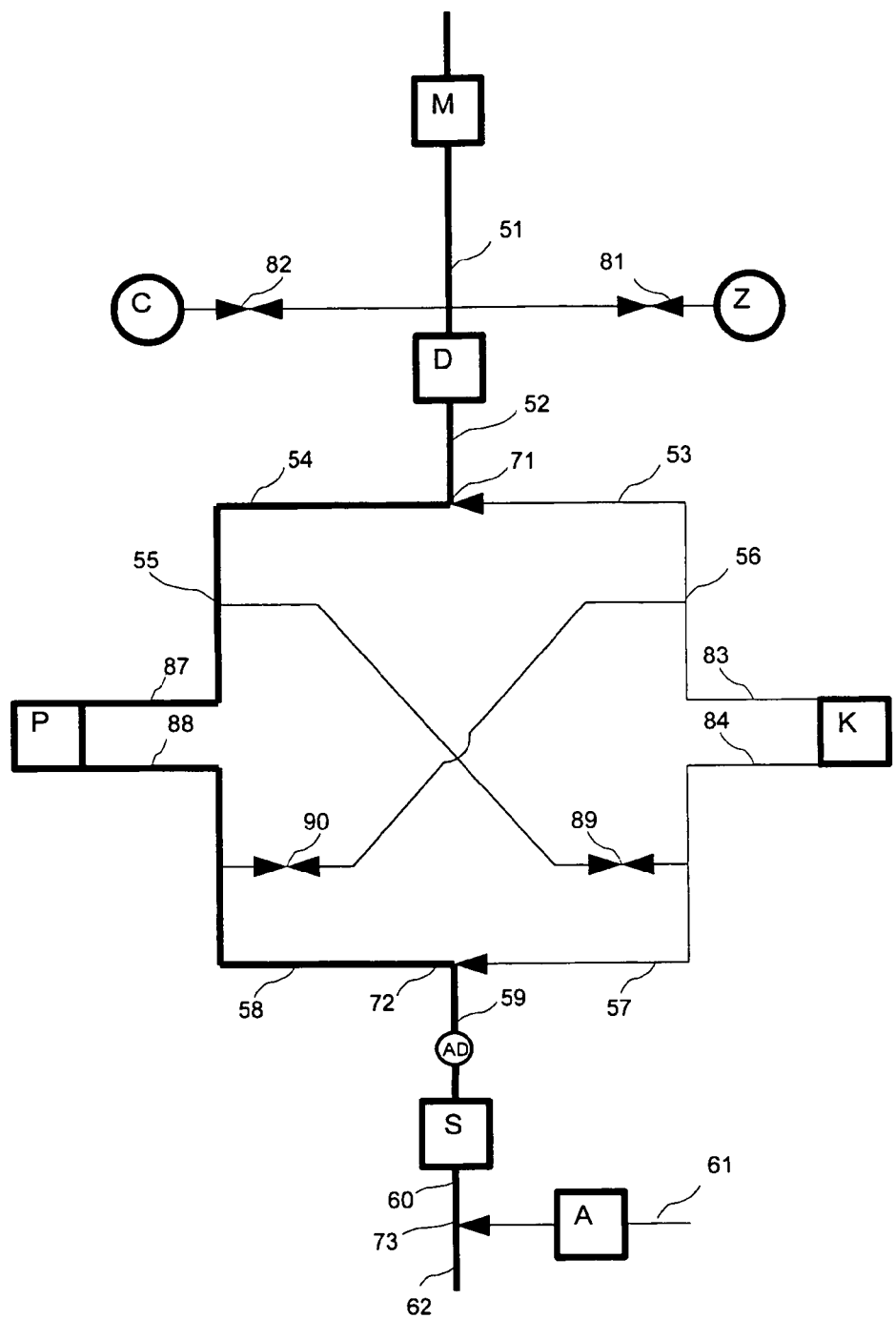
Figure 5:
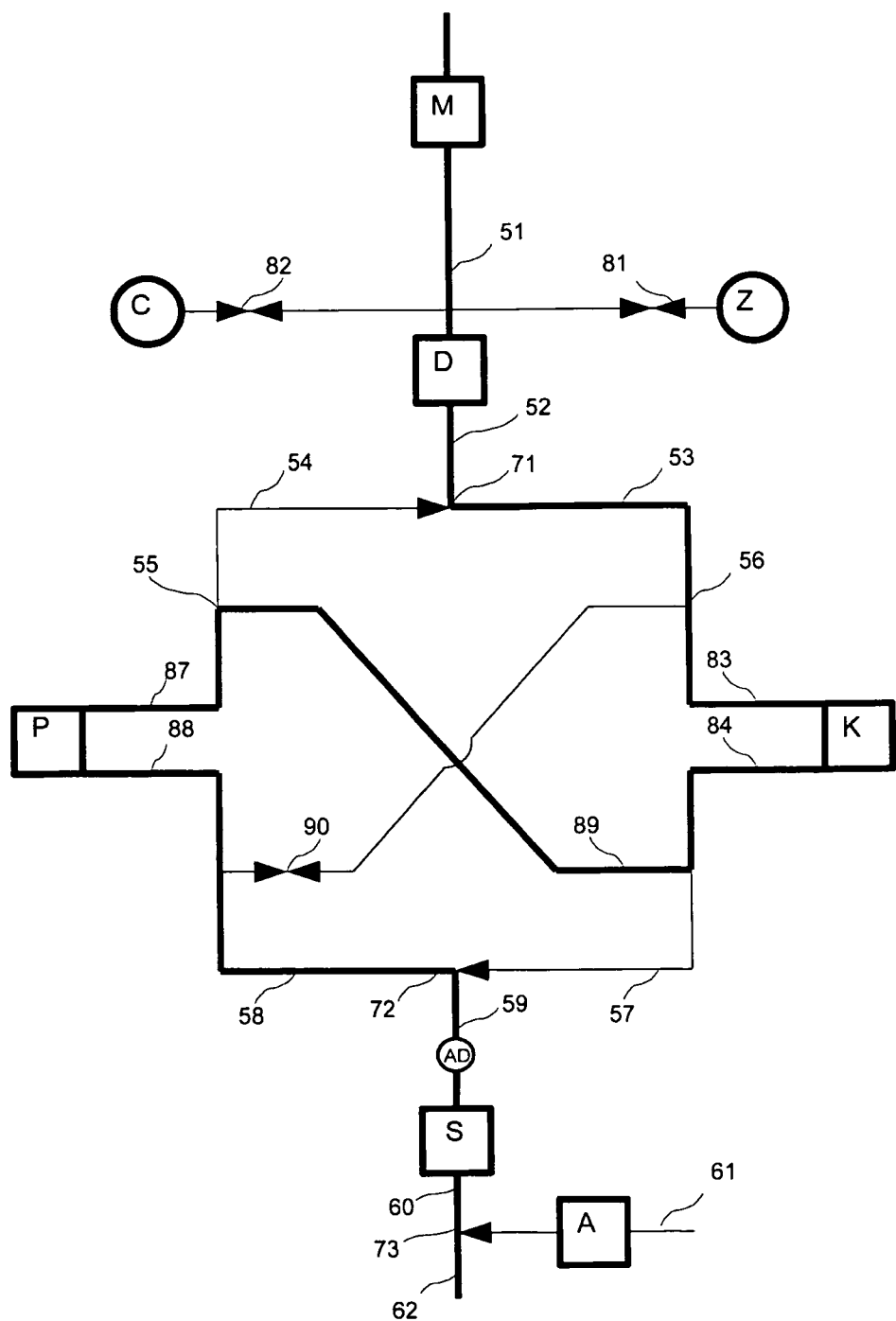
Figure 6:
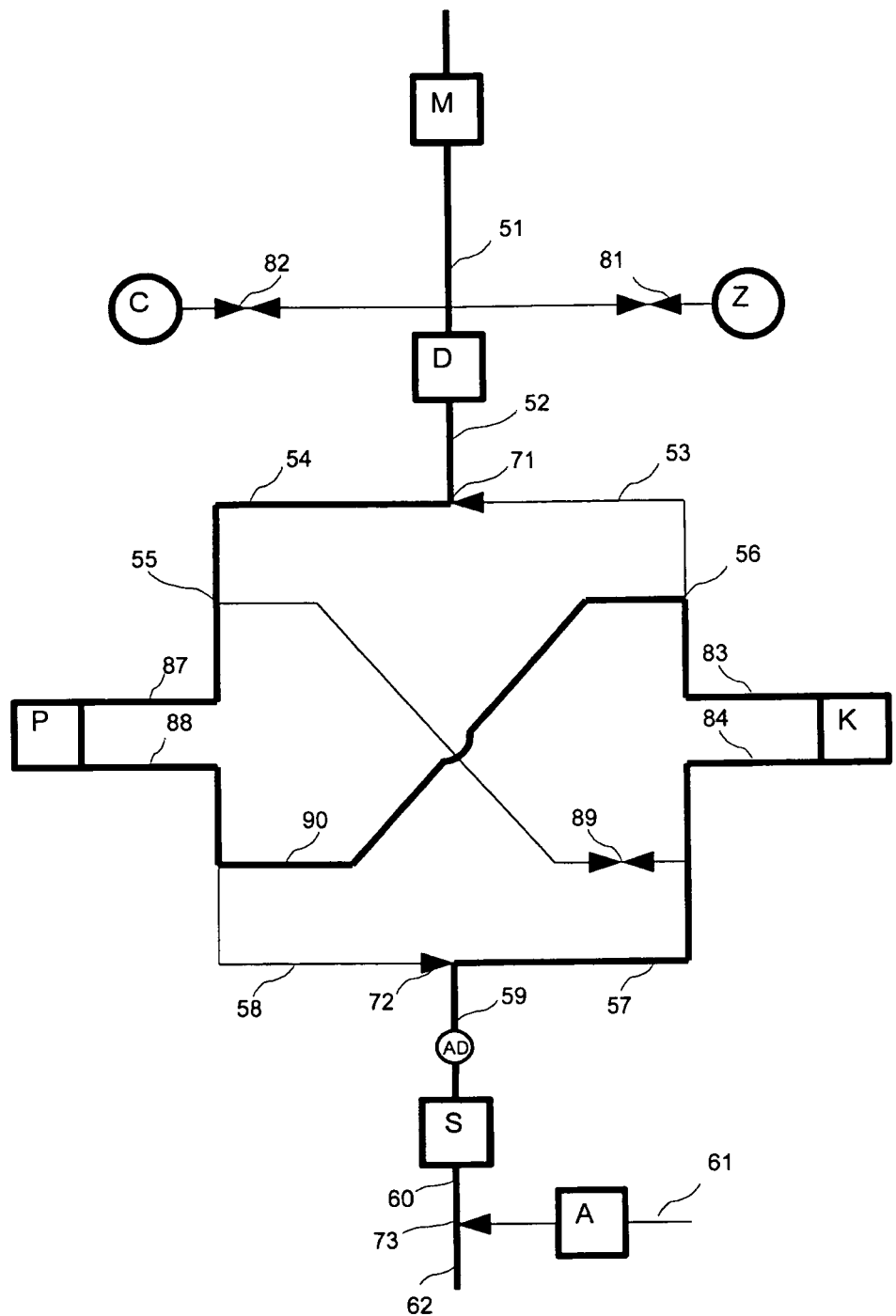
Figure 7:
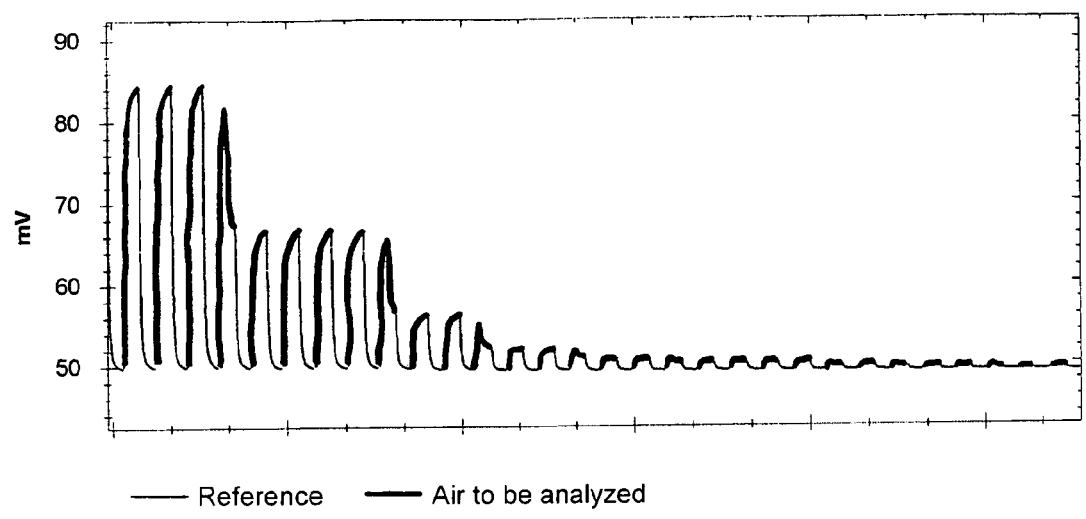
Figure 8:
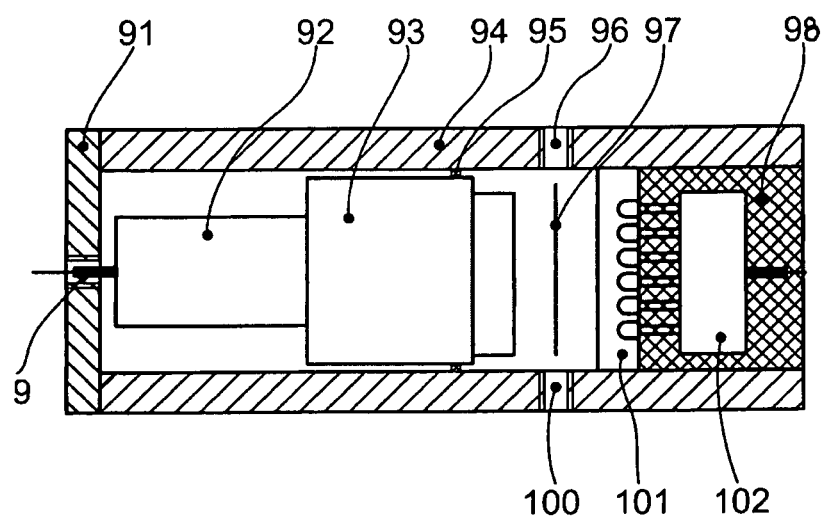
Figure 9:
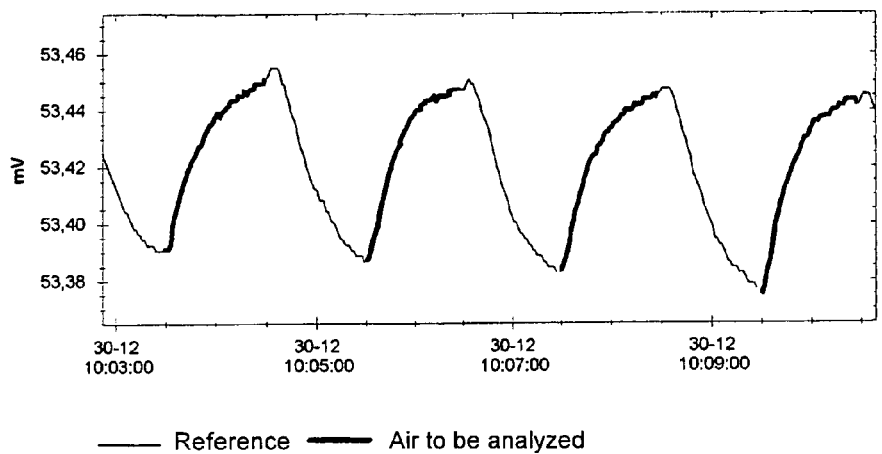
Figure 10:
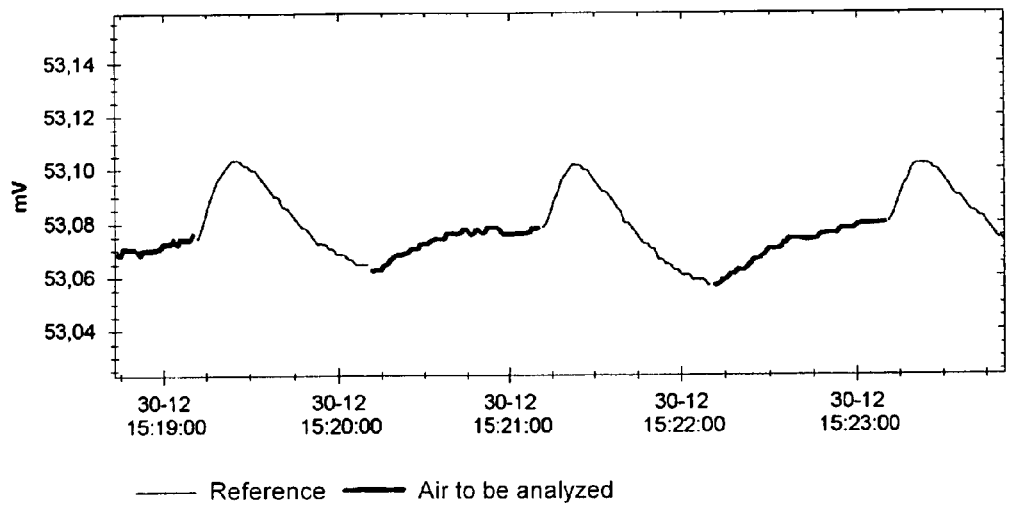
Figure 11:
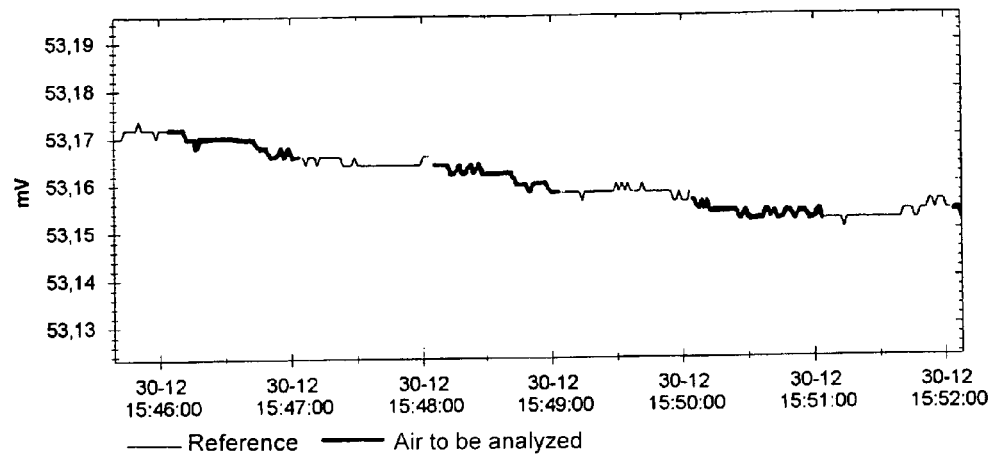
Figure 12:
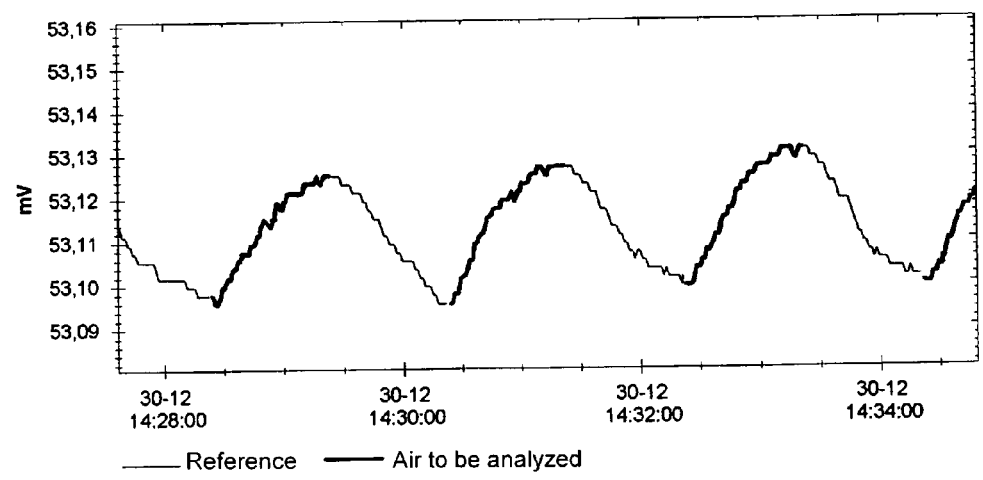
Figure 13:
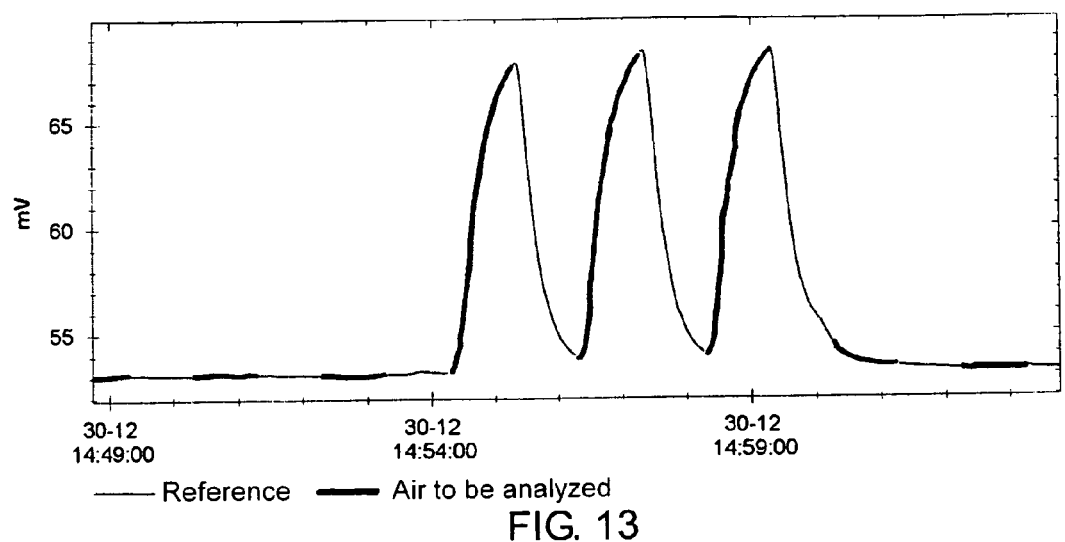

FIG. 1 is a schematic diagram of the measuring instrument according to the invention, FIG. 2 shows the switch positions of the magnetic valves for measuring the air to be analysed, FIG. 3 shows the routing of air from the compressed-air connection through the catalyst, FIG. 4 shows the routing of air from the compressed-air connection through the permeator, FIG. 5 shows the routing of air from the compressed-air connection through the catalyst and then the permeator, FIG. 6 shows the routing of air from the compressed-air connection through the permeator and then the catalyst, FIG. 7 shows the measurement curve progression for a typical measurement using dilution series, FIG. 8 shows a measuring chamber of a measuring instrument according to the invention, FIG. 9 shows the measurement curve progression for a measurement of activated-charcoal-treated compressed air, FIG. 10 shows the measurement curve progression for a measurement of slightly moistened zero air, FIG. 11 shows the measurement curve progression for a measurement of slightly moistened zero air after the compensator, FIG. 12 shows the measurement curve progression for a measurement of activated-charcoal-treated compressed air after the compensator, and FIG. 13 shows the measurement curve progression for a measurement of activated-charcoal-treated compressed air after the compensator with three inserted test-gas measurements.

The design of the measuring instrument is illustrated in FIG. 1. The valves 51, 81, 82, 89 and 90 are electrically actuated magnetic cut-off valves. The valves 71, 72 and 73 are electrically actuated magnetic 3/2 directional valves.

M is a compressed-air connection with a permanently adjusted pressure regulator between 1 and 14 bar, for example 7 bar.

C is test gas in a test-gas cylinder with a likewise permanently adjusted pressure regulator that typically reduces the pressure to 7 bar.

Z is zero air in a zero-air cylinder, again with a typical pressure reduction to 7 bar. The zero-air cylinder contains zero air and, in addition, a hydrocarbon with a concentration in the ppb or ppm range.

D is a flow limiter. This may be a flow restrictor made of sintered metal or simply a sapphire or ruby nozzle with an internal diameter preferably between 50 and 200 μm, for example an 80 μm internal diameter. The air flow rate is limited in this way to 2 litre/minute, for example, at a system pressure of 7 bar.

P is a permeator containing a permeation membrane. This is typically a short, closed piece of PTFE tube, filled with a hydrocarbon. Assuming a constant temperature and a constant air passage, a defined, constant hydrocarbon content is generated in the air flowing past by permeation.

K is an oxidation catalyst. This is a heated container filled with granulated copper manganate. It is manufactured by filling a stainless steel tube with 2 to 50 g of granulated copper manganate (commercially available in the catalyst industry), for example Carulite 300 from Carus. The oxidation temperature should not exceed 200° C. so that the heating required for the catalyst and the air to be oxidized remains acceptable from the equipment and energy-consumption aspects.

In this context, it must be remembered that lubrication oils and compressor oils used in industry contain sulphur-containing components that destroy the catalytic effect of precious metals routinely used in the automotive industry as oxidation catalysts for treating exhaust gases.

Whereas temperatures of above 600° C. prevail in the exhaust system of motor vehicles during operation and lead to detoxification of the catalyst again, the upper temperature limit of 200° C. specified here is not sufficient to detoxify the catalyst, i.e. to remove the sulphur components deposited on its surface.

Even at 200° C., stainless steel catalysts were in fact always found to have sufficient catalytic activity for the task in question; however, their useful service life is limited by poisoning. The service life can be substantially prolonged if a sulphur trap is fitted in front of the precious metal catalyst. Suitable substances for this purpose include granulated oxides of zinc, iron, copper or manganese. Metal wools made of copper, nickel and stainless steel were also used successfully, however, as well as Sorbens C-28 from United Catalysts. In the mobile variant, the catalyst is preferably a photocatalyst with a high proportion of titanium dioxide, which is illuminated by UV LEDs (wavelength 370-385 nm; from Lumitronix). DE 198 11 708 A1, for example, includes a description of how the photocatalyst is manufactured.

In the search for a suitable non-precious metal catalyst, trials showed that commercially available granulated copper manganate (Hopcalit) is extremely suitable and can already be used at temperatures as from 160° C. Although copper manganate, too, reacts with the sulphur compounds in the oils to form catalytically ineffective compounds, its absorbency is disproportionately higher and is sufficient for the task in question.

However, it was found that, as a metal oxide, copper manganate forms temperature-dependent reversible chemical bonds in the presence of air moisture and carbon dioxide. Air moisture particularly influences measurement values in the 10 μg oil/$m^3$ air range. The uptake of moisture by the catalyst material and its release into the treated air stream must therefore be taken into account in the design specifications for the measuring instrument.

AD is an air-moisture compensator. It is made by filling a small container or section of tube with materials of the kind typically used in adsorption dryers to take up moisture, such as a molecular sieve or aluminium oxide beads. However, the purpose of this compensator is not to dry the air stream flowing through it. Much rather, the compensator only works perfectly once it has reached the saturated state under the given conditions of temperature, moisture and pressure, with uptake and release of moisture being in equilibrium. It will release moisture into a dryer air stream or take up moisture from a moister air stream. As explained in the following description of how the measuring instrument works, magnetic valves are used to switch between air steams at intervals, thus evening out their slightly different moisture contents.

This compensator increases the instrument's measuring accuracy substantially, particularly in the lower measuring range, if a thermal oxidation catalyst consisting of copper manganese oxide (Hopcalit) is used as catalyst. As illustrated in FIG. 1 and FIG. 3, a typical, simplified embodiment of the measuring instrument according to the invention measures M against MK (the permeator is bypassed). Since the catalyst K continues to be heated during the compressed-air measuring phase M and the core temperature of the catalyst filling rises somewhat due to the interrupted airflow, the catalyst material dislodges small amounts of moisture. Switching over to the MK position causes air to flow over the catalyst again, and during this phase it initially releases the dislodged moisture that has collected. Towards the end of the MK phase, the core temperature of the catalyst sinks slightly and the catalyst again takes up small quantities of water.

S is a photoionization detector (PID) with a photon energy of 10.6 eV. Baseline-mocon and Alphasense manufacture suitable PIDs that respond with especially high sensitivity.

A is an activated charcoal tube for sampling according to DIN ISO 8573-5. Since the magnetic valve leading to this tube is controlled by the CPU, the amount of air that flows through the tube can be selectively specified and, using an optional switching position of the measuring instrument serving for its calibration, the value determined by the measuring instrument compared with the value obtained according to the DIN ISO method. However, use of this switching option, which routes air streams through the activated charcoal tube, is not essential to the functioning of the measuring instrument itself.

The measuring device of the invention overcomes the above-described difficulty of deducing the oil content in mg/$m^3$, as specified in DIN ISO 8573-1, from the signal strength of the PID sensor by having the percentage compositions of the oils to be detected, along with their molecular weights and response factors, stored in an internal database of the measuring instrument. These parameters are processed internally and the oil contents displayed with the units already converted. The user thus enters the name of the oil to be detected before starting a measurement, and then obtains the measuring result as mg of the respective oil/$m^3$ air. The instrument also communicates to the user the compressed-air class under which the result falls and an adjustable alarm-activation threshold.

FIG. 1 does not show the switch positions of the valves.

FIG. 2 shows the switch positions of the magnetic valves for measuring the air to be analysed. The lines which are shown bold compared to FIG. 1 show the path of the air through the measuring instrument. The switch positions shown here route the air to be analysed directly to the sensor. The closed side of the valves is always shown as a triangle. The air arriving at the sensor is designated here as M. If either the valve 82 or the valve 81 is opened instead of the valve 51, and no other changes are made to the routing, test gas C or zero air Z will be analysed at the sensor. For the sake of simplicity, the air then arriving at the sensor will be designated as C or Z below. Analogous designations will be used for the other air streams.

FIG. 3 shows the routing of air from M through the catalyst K, in which the hydrocarbons are oxidized. The air arriving at the sensor is designated here as MK. If either valve 82 or valve 81 is opened instead of valve 51, and no other changes are made to the routing, CK or ZK will be analysed at the sensor.

FIG. 4 shows the routing of air from M through the permeator P, in which the air stream is enriched with hydrocarbon from the permeation tube. The air arriving at the sensor is designated here as MP. If either the valve 82 or the valve 81 is opened instead of the valve 51, and no other changes are made to the routing, test gas C or zero air Z are analysed, with the difference that, this time, they have been enriched with hydrocarbon from the permeation tube. The air arriving at the sensor is designated as CP or ZP.

FIG. 5 shows the routing of air from M through the catalyst K and then through the permeator P. The air arriving at the sensor is accordingly designated as MKP. If either the valve 82 or the valve 81 is opened instead of the valve 51, and no other changes are made to the routing, air designated as CKP or ZKP arrives at the sensor.

FIG. 6 shows the routing of air from M through the permeator P and then through the catalyst K. The air arriving at the sensor is accordingly designated as MPK. If either the valve 82 or the valve 81 is opened instead of the valve 51, and no other changes are made to the routing, air designated as CPK or ZPK arrives at the sensor.

The principle according to which measurements are performed with the instrument of the invention is that, at given intervals, the valves are switched to and fro between at least two of the switch positions described above. The value measured by the sensor for any one particular air stream takes some 10 to 120 s to stabilize. This has to do with the fact that the sensor is protected against dust by a membrane and the concentrations on either side must first be equalized by diffusion.

Especially during an initial phase of 1-3 days, it is possible that the catalyst will release a little moisture, continuously yet to a decreasing extent, and thus falsify the measuring result. If one switches to and fro between Z (zero air) and ZK (zero air treated in the catalyst) at intervals of, say, 90 s, one obtains a voltage difference which, due to the release of moisture by the catalyst, may lead to a higher ZK value than the Z value—in other words, a negative result. The higher air moisture in ZK may thus cause a slightly higher measuring result. This "negative" value of the difference in measuring results can be set on the measuring instrument as the moisture-calibration value, i.e. used to compensate for measuring errors caused by moisture release from the catalyst material.

If one switches to and fro between positions C and CK at intervals of, say, 90 s, one obtains a voltage difference that can be used for calibration purposes, a higher voltage being obtained for C and a lower for CK. If the concentration, the sensitivity of the sensor as specified by the manufacturer and the chemical nature of the test gas have been set on the instrument in advance, the instrument will then adopt the value found as calibration factor.

If one switches to and fro between C and Z at intervals of, say, 90 s, one obtains a voltage difference that should correspond to the change between C and CK but will only do so if the catalyst K is fully functional. It is thus possible to check whether the catalyst is in proper working order by means of this comparison.

If one switches to and fro between positions C and Z (or C and CK) in such a manner that per cycle, for example, first CK remains open for 45 s and then, for the next 45 s, one switches to and fro every second between C and CK, one obtains only half the value of the concentration for C. With another setting, for example 45 s CK followed by 45 s during which one alternates between 1 s C and 2 s CK, one obtains ⅓ of the value of the concentration of C as measuring result, etc.

This component of the invention thus permits creation of a formula describing the dependence of the measuring result on concentration for purposes of checking the linearity. To this end, one can perform the following series of measurements: "0C-10CK vs. CK"; "1C-9CK vs. CK"; "2C-8CK vs. CK" to . . . "9C-1CK vs. CK"; "10C-0CK vs. CK". These measuring results can then be used to determine and store a linearisation formula. The instrument is able to arbitrarily check the validity of this linearisation function according to what has just been said.

This linearisation formula enables the instrument to correct the values measured for the gas to be analysed M against MK. The instrument is also able to check whether the linearisation formula found for C also applies to M, for example via a dilution series of M-MK vs. MK according to the same scheme as described in the section above for C-CK vs. CK.

The above analyses of C and Z and of their catalytically treated follow-on gases CK and ZK necessitate the use of gas cylinders, as test gases and zero air are usually supplied in compressed-gas cylinders.

However, for the end users of measuring instruments, gas cylinders are usually too awkward and difficult to handle.

It is thus within the scope of this invention to use permeators instead of gas cylinders for calibration purposes, and to generate the calibration gas from the air to be analysed M by means of a permeator. Permeation tubes can be purchased already calibrated, for example from Kin-Tec, USA. It is also possible to re-calibrate the permeation tube with test gas C.

It is also possible to generate a dilution series by means of the permeator P. It would be wrong, however, to measure MK for 45 s per cycle and then, for the second 45 s of the cycle, to alternate between, for example, 0.3 s MKP and 0.7 s MK in order to generate, for example, 30% of the permeator tube's emission concentration, because permeator tubes continue to emit even when the gas flowing over them is briefly interrupted. Intermittent interruptions in the airflow through the permeator P cause a concentration increase within the permeator, and when the airflow is resumed, correspondingly higher concentrations will be emitted.

Dilution series by means of a permeator are therefore generated by measuring MPK (FIG. 6) for, say, 45 s per cycle and then, for the next 45 s, alternating between, e.g., 0.9 s MPK (FIG. 6) and 2.1 s MKP (FIG. 5) in order to generate, for example, 70% of the permeator's emission concentration. In this way, the unwanted permeator emissions are oxidised during the pauses and do not accumulate as they would with the procedure described in the previous paragraph.

To measure the full value of the concentration, one would simply switch between MPK (FIG. 6) and MKP (FIG. 5) at, say, 45 s intervals.

By virtue of the long service life (up to several years) of permeation tubes, this solution thus provides a new, simple and cost-efficient method for routine, automatic calibration (including a linearisation function) of the measuring instrument.

The permeation tubes can be re-calibrated now and then by way of a comparative measurement using a test-gas cylinder to be connected thereto; the test gas or air from the permeator can be diluted according to the method described previously in such manner that they lie within the same concentration range, linearisation errors accordingly being prevented.

If, in order to measure the analyte gas, one switches to and from between M and MK at intervals of, say, 90 s, one obtains a voltage difference from which the measuring instrument calculates the content of the respective hydrocarbon entered. The calculation is based on the moisture-correction factor, calibration factor, response factor and the type of hydrocarbon.

The instrument provides the opportunity of checking whether the measuring result is already within a non-linear measuring range or whether the automatically linearised value is correct. For this purpose, a dilution series is generated automatically at intervals. The dilution series is generated by measuring MK (FIG. 3) for, say, 45 s per cycle and then, for the next 45 s, alternating between, e.g., 0.9 s MK (FIG. 3) and 2.1 s M (FIG. 2) in order to generate, for example, 70% of the full value.

In the measuring range below 2 ppb, it is difficult to use a correct linearisation formula; this is because the deviation from linearity increases logarithmically with decreasing signal strength, with the result that tiny measuring inaccuracies are correspondingly increased. Provision is therefore made for the signal for the actual measurement and for the reference measurement to be increased by an identical amount. This has the effect of shifting the measurement into a higher signal-strength range and producing a more accurate measuring result.

Thus, instead of measuring the small difference between a very low M (air to be analysed) and MK (as zero reference), one measures the difference between MP (FIG. 4) and MKP (FIG. 5) as zero reference. Equal quantities of hydrocarbon emitted from the permeator are added in this case to both the air to be analysed M and the catalytically treated air MK. Thanks to appropriate permeator-tube selection, the amount of hydrocarbon emitted from the permeator P is much higher here than the concentration of hydrocarbons in M. By way of a dilution series of MP-MKP vs. MKP, e.g. alternating between 1 s MP and 4 s MKP for 45 seconds and then measuring MKP for 45 seconds (desired concentration: 0.2 M), the improvement in linearisation can be checked.

Despite the sluggishness of the air exchange across the membrane protecting the sensor, a slightly sinusoidal signal progression, which can be smoothed mathematically by averaging, is obtained with the fast, second-wise to-and-fro switching during a measuring phase.

The switch duration for each switching cycle can be set manually on the instrument. However, the instrument is also able to automatically calculate the optimal switching instant from the generated measuring points and to switch the valves accordingly.

A temperature of at least 160° C. is required for the catalytic oxidation of hydrocarbon-containing air. Especially for a portable form of the instrument according to the invention, heating to this temperature with (re-chargeable) batteries limits operation to a short period. A further difficulty is the lengthy heating-up period. A simplified version of the instrument therefore uses an activated-charcoal adsorber instead of the catalyst.

Since activated charcoal adsorbs water as well as hydrocarbons, the alternative use of activated charcoal reduces the accuracy of the corresponding measurements. The adsorptive capacity of activated charcoal also decreases in uncontrollable manner over time.

It was described earlier on how measuring accuracy can be increased by enriching both sides of a referencing measurement by the same amount of hydrocarbons from the permeator, because the measurement is then shifted into the linear range. The influence of air moisture on the measuring result is also reduced by doing this. Measurements carried out with activated charcoal adsorption instead of catalysis can also be improved substantially in this way by means of permeation.

It is thus also possible to obtain good measurement results with the circuit MP (FIG. 4) vs. MPK' (FIG. 6, but with activated charcoal K' instead of the catalyst K). The many possible combinations described above and illustrated in FIG. 2-FIG. 6 for the catalyst K apply equally to K', i.e. the activated charcoal adsorber.

There is also a simplified version of the instrument that does not include a permeator and that operates only with a catalyst and/or only with an activated charcoal adsorber.

However, the above-described linearisation functions based on dilution series can also be performed with these simplified instruments.

The measuring instrument according to the invention can be pre-programmed with the parameters for the substances contained in commercial oils to be analysed, and these parameters can be used as a calculation basis.

In addition, GC/MS analyses are prepared for commercial compressor oils and, taking into account the respective proportions of the individual components in oil, their respective molecular weights, and their response factors, pre-programmed as constants.

In case of doubt, the measuring result can be confirmed using an established method for better acceptance. To this end, a measuring result is simultaneously determined according to DIN ISO 8573-5 by means of a hydrocarbon collection tube and analysis by a certified laboratory, and if desired by the user, entered in an input box as "DIN-ISO calibration value".

The measuring method of this measuring instrument makes it possible, by means of alternating valve circuits, to generate signal differences and thus to obtain measuring results, and simultaneously a) to compensate for sensor drift,
b) to compensate for varying moisture content of the air to be analysed,
c) to monitor the catalyst for proper functioning,
d) to increase the measuring accuracy by admixing,
e) to monitor the permeation tube for correct functioning, and
f) to permit permanent comparison with the measuring method according to DIN ISO 8573-5.

In an extended version of the measuring instrument, the instrument forms a structural unit with a catalytically oxidative treatment system for removing hydrocarbons or reductive gases from large volumes of used air or compressed air. In a unit of this kind, 1 $m^3$/min, for example, flows through the catalyst of the treatment system for used compressed air and 2 l/min through the measuring instrument's own small catalyst. The advantage is that the measuring instrument's small catalyst is installed within the large catalyst and is heated up at the same time. In practice, this simply involves installing a separating tube with its own output in the heated catalyst bed.

The treatment system contains a heat exchanger for recovering the thermal energy used and for heating up the incoming hydrocarbon-containing air. Whereas plate heat exchangers are preferred for larger variants of the treatment system, double-pipe heat exchangers are given preference in smaller variants.

Catalyst quantities and the quantities of air flowing through the treatment system and the measuring instrument are selected such that the load on the measuring instrument's catalyst is much lower. For the measuring instrument's catalyst, the ratio of hydrocarbon to catalyst should preferably not exceed one tenth of that for the treatment system's catalyst.

As soon as the oxidative capacity of the treatment system's catalyst begins to decrease with time, the hydrocarbon values for the stream of air to be analysed and for the stream of reference air, which were originally equal, will differ increasingly. This difference is determined by the measuring instrument, and, in this way, the decreasing performance of the catalyst in the treatment system is detected and monitored by the measuring instrument.

FIG. 7 shows the measuring curve progression of a typical dilution-series measurement for C-CK vs. CK After the magnetic valve is switched to C-CK, the curve rises steeply until the particular dilution value for C-CK is reached; switching to CK causes the measurement signal to decrease again. The level of dilution was increased each time after the 3rd, 8th, 11th, 14th, 17th, 22nd, 24th and 28th measurement, i.e. the proportion of time for which C is open becomes smaller and smaller. The first measurement obtained in each case after switching over to the next dilution should be ignored.

Additional subject matter of this invention is an embodiment in which the photocatalyst forms a structural unit with the photoionization detector as a measuring chamber (see FIG. 8). This measuring chamber 91 is preferably designed such that, by installing a photoionization detector 93 with an AD converter 92 and a UV photo unit 98, a hollow space of <1 $cm^3$ volume is formed, which contains a photocatalytically active film 97. The film 97 is illuminated through a chamber wall 101 made of transparent plastic by a plurality of UV LEDs. Another chamber wall is formed by the front of the photoionization detector 93. The gas with which this chamber is filled is exchanged periodically via the openings 96 and 100, which are equipped with flow resistors.

FIG. 9 shows a typical measurement performed on compressed air with this variant of the measuring instrument.

The compressed air from an oil-driven compressor (7 bar) was pre-treated with a refrigerant-type dryer, pre-filter, water separator and activated charcoal. The residual-oil vapour content of this compressed air is generally substantially below 0.01 mg/$m^3$ normal air. The rise in measurement signal during the compressed-air phase M is followed by a decrease in the signal during the catalytic-air phase MK. At the start of the catalytic-air phase, a distinct "bump" is evident. The following example shows that this bump is caused by the release of water. If, using the same setup, one measures slightly moistened zero air instead of the described compressed air, a very large bump is formed, which is followed, towards the end of the catalytic-air phase, by a very deep valley. This is shown in FIG. 10. The signal increases again during the compressed-air phase. Although this zero air contains no hydrocarbons, an artificial positive signal is obtained due to the behaviour of the Hopcalit catalyst. At the start of the catalytic-air phase, released water causes a bump; towards the end, water is adsorbed and the signal decreases accordingly.

This effect is eliminated through use of the compensator AD. In FIG. 11, the effect of the compensator on the measurement performed on moistened zero air and represented by the curve of FIG. 10 is evident. The value obtained now is below the sensor's limit of sensitivity, with only a noise signal of about 2 mV being evident that is caused by the AD converter's resolution. Only sensor drift changes the measurement signal. The drift-compensated measurement value shown is below 0.001 mg/m$^3$ In FIG. 12, the compensator's effect on the signal obtained for the measurement on compressed air as per FIG. 9 is evident. Here, a quantity of 2 g porous aluminium oxide beads were used—to compensate a quantity of 5 g granulated Hopcalit—in an 8 mm stainless steel tube of 30 cm length, heated from the exterior to 200° C. With this quantity of 2 g, the bump has already disappeared completely.

The question arises here as to the extent to which the compensator also compensates, in undesirable manner, for the residual oil content. Surprisingly, it was found that undesirable "compensation" of the oil vapour was minimal, i.e. the oil vapour is able to pass through the compensator material without any, notable storage effect. Porous materials of this kind apparently only work as useful adsorbers at substantially higher concentrations. To confirm this, measurements as illustrated in FIG. 13 were performed. During a compressed-air measurement (<0.01 mg/m$^3$) with correspondingly low ppb hydrocarbon concentrations, three measuring cycles were performed with the measuring instrument on a substantially more concentrated test gas containing 0.5 ppm hydrocarbons. FIG. 13 shows the comparatively weak signals obtained for the compressed air, then three strong signals for the test gas, followed immediately once more by the weak compressed-air signals; the essential point regarding the latter is that the signal for hydrocarbon content is not elevated following the strong measurement signals. Since the scale for the curve of FIG. 13 is much smaller, optical recognition of the change in signal strength for the compressed-air measurement is no longer possible from the curve. The signals to the left and right of the three strong signals in FIG. 13 do, however, correspond to those in FIG. 12.

The invention claimed is:

1. A measuring instrument for detecting the content of oil, hydrocarbons and oxidizable gases in air or compressed air, wherein the measuring instrument has an air or compressed-air connection and, connected thereto, a flow limiter to which a thermal oxidation catalyst is connected that is connected in turn with a photoionization detector, switchable means being provided for routing the air or compressed air over the oxidation catalyst or past the oxidation catalyst directly to the photoionization detector, wherein a switchable test-gas inlet is fitted between the air or compressed-air connection and the flow limiter, and wherein the measuring instrument is configured to catalytically oxidize a variable proportion of the hydrocarbons and, in this way, generate dilution series for the purpose of carrying out a referencing measurement while hydrocarbon-containing air or compressed air is being analyzed.

2. The measuring instrument according to claim 1, wherein, in addition to the oxidation catalyst, at least one permeator for releasing a temporally constant, defined amount of hydrocarbon is installed, with switchable means being provided for routing the air or compressed air via the permeator or past the permeator directly to the photoionization detector.

3. The measuring instrument according to claim 1, wherein a switchable test-gas inlet is fitted between the air or compressed-air connection and the flow limiter.

4. The measuring instrument according to claim 1, wherein a switchable zero-air inlet is fitted between the air or compressed-air connection and the flow limiter.

5. The measuring instrument according to claim 1, wherein a switchable connection to an activated-charcoal tube is provided subsequent to the photoionization detector.

6. The measuring instrument according to claim 1, wherein an air-moisture compensator is fitted upstream of the photoionization detector.

7. A method for detecting the content of oil, hydrocarbons and oxidizable gases in air or compressed air using a measuring instrument having an air or compressed-air connection and, connected thereto, a flow limiter to which a thermal oxidation catalyst is connected that is connected in turn with a photoionization detector, switchable means being provided for routing the air or compressed air over the oxidation catalyst or past the oxidation catalyst directly to the photoionization detector, wherein a switchable test-gas inlet is fitted between the air or compressed-air connection and the flow limiter, and wherein, for the purpose of carrying out a referencing measurement while hydrocarbon-containing air or compressed air is being analyzed, a variable proportion of the hydrocarbons is catalytically oxidized and, in this way, dilution series are generated.

8. The method according to claim 7, wherein, for the purpose of carrying out a referencing measurement while hydrocarbon-containing air or compressed air is being analyzed, a variable proportion of zero air is mixed with the hydrocarbon-containing air and, in this way, dilution series are generated.

9. A method for detecting the content of oil, hydrocarbons and oxidizable gases in air or compressed air using a measuring instrument having an air or compressed-air connection and, connected thereto, a flow limiter to which a thermal oxidation catalyst is connected that is connected in turn with a photoionization detector, switchable means being provided for routing the air or compressed air over the oxidation catalyst or past the oxidation catalyst directly to the photoionization detector, wherein a switchable test-gas inlet is fitted between the air or compressed-air connection and the flow limiter, wherein an air-moisture compensator is fitted upstream of the photoionization detector, wherein, for the purpose of carrying out a referencing measurement while hydrocarbon-containing air or compressed air is being analyzed, a variable proportion of zero air is mixed with the hydrocarbon-containing air and, in this way, dilution series are generated, and wherein the zero air is catalytically treated and, in order to increase the measuring accuracy, both the hydrocarbon-containing air to be analyzed and the catalytically treated air or the zero air are enriched by way of a permeator with equal amounts of hydrocarbon so as to shift the measuring range into the linear measuring range.

* * * * *